US012758665B2

(12) United States Patent
Leasure et al.

(10) Patent No.: US 12,758,665 B2
(45) Date of Patent: Oct. 13, 2026

(54) ANTI-BIOFOULING WATER IN FUEL SENSOR, ANTI-BIOFOULING WATER SUMP AND RESERVOIR AND METHOD OF RETROFITTING WATER SUMPS AND RESERVOIRS TO INCORPORATE ANTI-BIOFOULING SYSTEM

(71) Applicant: Schroeder Industries, LLC, Leetsdale, PA (US)

(72) Inventors: Chris Leasure, Sewickley, PA (US); Kelly Coyne, Leetsdale, PA (US)

(73) Assignee: SCHROEDER INDUSTRIES, LLC, Leetsdale, PA (US)

( * ) Notice: Subject to any disclaimer, the term of this patent is extended or adjusted under 35 U.S.C. 154(b) by 372 days.

(21) Appl. No.: 18/378,131

(22) Filed: Oct. 9, 2023

(65) Prior Publication Data

US 2024/0157004 A1 May 16, 2024

Related U.S. Application Data

(63) Continuation of application No. PCT/US2022/024279, filed on Apr. 11, 2022.
(Continued)

(51) Int. Cl.
*A61L 2/10* (2026.01)
*A61L 2/26* (2006.01)
(Continued)

(52) U.S. Cl.
CPC .................. *A61L 2/10* (2013.01); *A61L 2/26* (2013.01); *B01D 17/045* (2013.01); *B01D 17/12* (2013.01);
(Continued)

(58) Field of Classification Search
CPC .......... A61L 2/10; A61L 2/26; A61L 2202/11; A61L 2202/14; B01D 17/045;
(Continued)

(56) References Cited

U.S. PATENT DOCUMENTS

| | | | |
|---|---|---|---|
| 8,865,004 | B2 | 10/2014 | Eberle et al. |
| 2011/0174717 | A1 | 7/2011 | Braunheim et al. |
| 2020/0017351 | A1 | 1/2020 | Schultz et al. |

FOREIGN PATENT DOCUMENTS

| | | |
|---|---|---|
| WO | 2003/065032 | 8/2003 |
| WO | 2022/217149 | 10/2022 |

*Primary Examiner* — Georgia Y Epps
*Assistant Examiner* — Hanway Chang
(74) *Attorney, Agent, or Firm* — Blynn L. Shideler; Krisanne Shideler; BLK Law Group

(57) ABSTRACT

A sump of a water coalescing filter includes a sump space, a drain coupled to the sump space, a water sensor coupled to the sump space to periodically activate the drain and at least one UVC light source illuminating the water sensor within the sump space. An anti-biofouling reservoir for an industrial fluid includes a reservoir space and sterilization zone or sump space as a lower portion thereof, and preferably a drain is coupled to the sterilization zone, a water sensor coupled to the sterilization zone that is used to periodically activate the drain and at least one UVC light source illuminating the fluid within the sterilization zone. An anti-biofouling water in fuel sensor includes a sensor body having a pair of spaced probes and at least one UVC light source configured for illuminating the probes.

18 Claims, 2 Drawing Sheets

Related U.S. Application Data

(60) Provisional application No. 63/262,154, filed on Oct. 6, 2021, provisional application No. 63/173,226, filed on Apr. 9, 2021.

(51) Int. Cl.
*B01D 17/04* (2006.01)
*B01D 17/12* (2006.01)
*C02F 1/32* (2023.01)
*G05D 9/12* (2006.01)

(52) U.S. Cl.
CPC ................ *C02F 1/32* (2013.01); *G05D 9/12* (2013.01); *A61L 2202/11* (2013.01); *A61L 2202/14* (2013.01); *C02F 2201/3222* (2013.01); *C02F 2303/04* (2013.01); *C02F 2303/20* (2013.01)

(58) Field of Classification Search
CPC .... B01D 17/12; C02F 1/32; C02F 2201/3222; C02F 2303/04; C02F 2303/20; G05D 9/12
See application file for complete search history.

FIG. 3
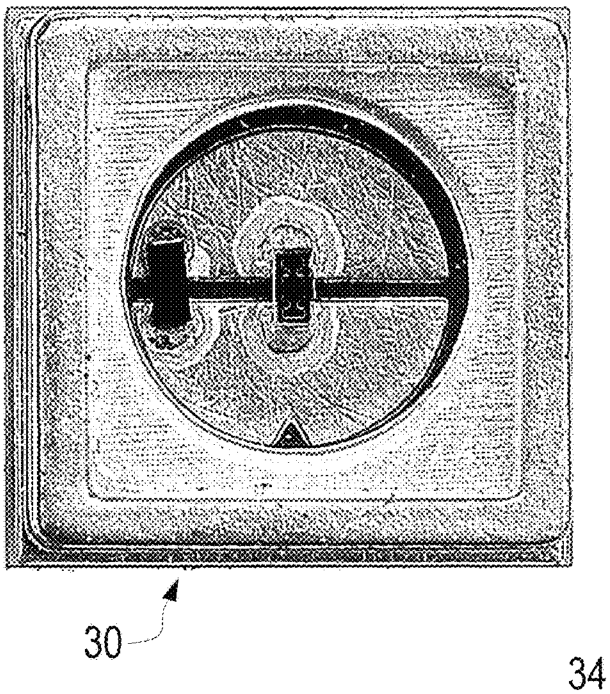
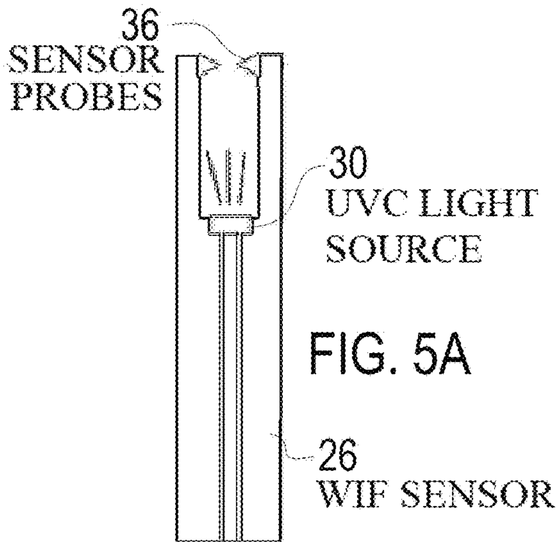
FIG. 5A
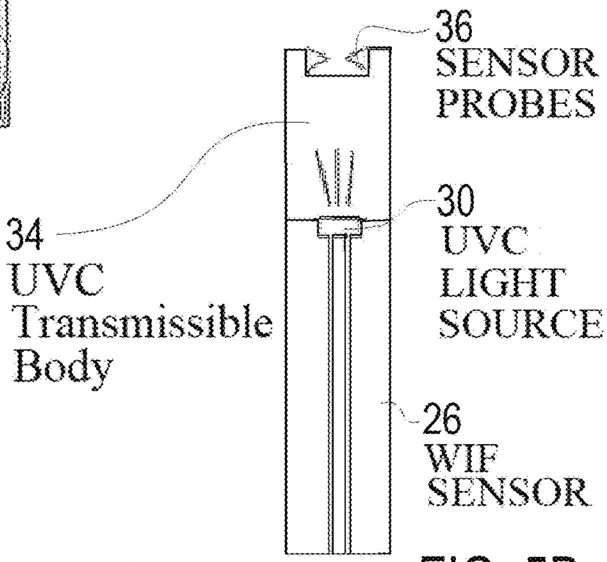
FIG. 5B
FIG. 4
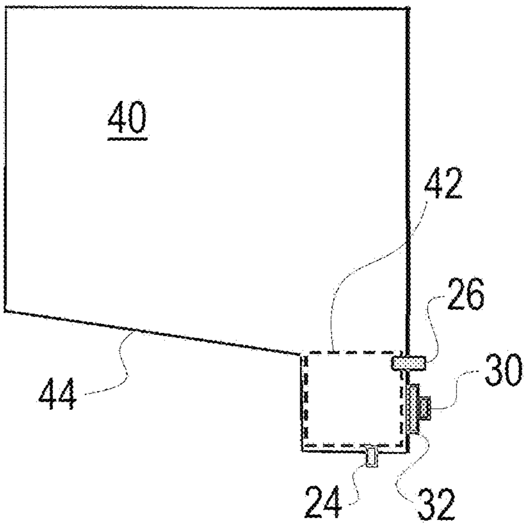

ANTI-BIOFOULING WATER IN FUEL SENSOR, ANTI-BIOFOULING WATER SUMP AND RESERVOIR AND METHOD OF RETROFITTING WATER SUMPS AND RESERVOIRS TO INCORPORATE ANTI-BIOFOULING SYSTEM

RELATED APPLICATIONS

This application is a continuation of International Patent Application Serial Number PCT/US2022/024279 filed Apr. 11, 2022 titled "Anti-Biofouling Water in Fuel Sensor, Anti-Biofouling Water Sump and Reservoir and Method of Retrofitting Water Sumps and Reservoirs to Incorporate Anti-Biofouling System" which published Oct. 13, 2022 as publication number WO 2022/217149, which application and publication are incorporated herein by reference.

International Patent Application Serial Number PCT/US2022/024279 claims the benefit of Provisional Application Ser. No. 63/173,226 filed Apr. 9, 2021 and 63/262,154 filed Oct. 6, 2021, which applications are incorporated herein by reference.

BACKGROUND INFORMATION

1. Field of the Invention

The present invention relates to primarily to anti-biofouling in water in fuel sensors and in a water sump in a water separation assembly of a fuel, hydraulic fluid, or industrial fluid, or to anti-biofouling in the reservoir for a fuel, hydraulic fluid, or industrial fluid.

2. Background Information

Water is a well-known problem in fuels causes tank and plumbing corrosion, and poor engine or system performance. In order to minimize these issues there are fuel treatment additives, draining the water from the bottom of the fuel reservoir and the use of water coalescing filters that effectively remove water from fuel. Water removed from fuel in a coalescing filter generally collects it in a sump that is periodically drained as signaled by a water sensor, generally a water in fuel (WIF) sensor.

A WIF (Water In Fuel) sensor is used to detect water in fuel in coalescing filter sumps among other uses. The basic WIF sensor utilizes two metallic probes separated by a short distance which creates an open circuit and which normally signals an "open" circuit. When the probe is exposed to water, the signal passes through the water and closes the circuit which signals the presence of water, as water is more conductive than fuel or industrial fluids.

The conventional WIF sensor is susceptible to bio-fouling due to microbial growth in the water and/or fuel. The microbial growth can cover the sensor and prevent the operating of the sensor by creating an insulating barrier between the sensor and the water, preventing the circuit from closing. This creates the problem where the system does not sense the presence of water, where the sump will not drain, thereby preventing proper operation of the coalescing filter.

Water also creates a similar problem for hydraulic fluid and industrial fluids generally. Hydraulic fluid within the meaning of this application reference petroleum or natural oil based fluids. Water in hydraulic fluid is known to deplete some additives and react with others to form corrosive by-products which attack some metals. Water in hydraulic oil is known to reduce lubricating film-strength, which leaves critical surfaces vulnerable to wear and corrosion. Water in hydraulic oil is known to reduce filterability and clogs filters. Water in hydraulic fluid is known to increase air entrainment ability and the likelihood of cavitation occurring. Water in hydraulic fluid is also addressed, in part, with the use of water coalescing filters that remove water from fuel, where it collects it in a sump, which is periodically drained as signaled by a water sensor, which may also be a water in fuel (WIF) sensor.

There are some petroleum or natural oil based fluid systems used in industry that are not categorized as fuels or hydraulic fluids, per se, such as for example a petroleum or natural oil based cutting fluid, and these will be categorized herein as industrial fluids. Whether a fuel system, hydraulic fluid system or industrial fluid system, the fluid flows from a reservoir, or tank, and except for the fuel system, the fluid will return to the reservoir. Additionally, as noted above to address the water problem the fluid is directed water coalescing filters that remove water from fuel, where it collects it in a sump that is periodically drained as signaled by a water sensor, which may also be a water in fuel (WIF) sensor.

Biofouling, or biological fouling is the accumulation of micro-organisms, plants, algae, or small animals where it is not wanted on surfaces, devices such as water inlets, pipework, grates, ponds, and rivers that cause degradation to the primary purpose of that item. In the sump environment, bacteria growth in the water can coat the water sensor over time and cause it to fail to sense water in the sump, in turn causing the automatic drain feature of the sump to fail. With the sump not draining, the sump will overfill with water and will force water to travel downstream past the filter. Bacteria in the fuel/water will feed on the fuel and cause it to degrade and increase the acidity of the fuel. FIG. 1A shows biofouling in a sump space and FIG. 1B shows biofouling of a sump water in fuel sensor preventing proper operation.

There is a need to minimize biofouling of water level sensors in a sump of a water coalescing filter that is periodically drained by the operation of the water sensor.

SUMMARY OF THE INVENTION

One embodiment of the present invention provides an anti-biofouling reservoir for a fuel, hydraulic fluid, or industrial fluid including a reservoir space, sterilization zone as a lower portion of the reservoir space, a drain is coupled to the sterilization zone for periodic draining of the sterilization zone, a water sensor coupled to the sterilization zone that is used to periodically activate the drain, and at least one UVC light source configured for illuminating the fluid within the sterilization zone.

The anti-biofouling reservoir for a fuel, hydraulic fluid, or industrial fluid according to the invention may provide wherein the water sensor includes sensor probes positioned so as to be illuminated by at least one UVC light source to provide for anti-biofouling of the sensor probes. The anti-biofouling reservoir may include a bottom surface of the reservoir space is sloped to guide fluid to the sterilization zone. The anti-biofouling reservoir for a fuel, hydraulic fluid, or industrial fluid according to the invention may provide wherein the sterilization zone is sized to allow for sterilization of the entire zone by the at least one UVC light source, and wherein the at least one UVC light source is configured to be operated intermittently.

The anti-biofouling reservoir for a fuel, hydraulic fluid, or industrial fluid according to the invention may provide wherein at least one UVC light source is integrated with the water sensor and formed in a sensor body and directed at sensor probes, and wherein the UVC light source is integrated with the water sensor has light directed through a UVC trans-missive body.

One embodiment of the present invention provides a sump of a water coalescing filter including a sump space; a drain coupled to the sump space for periodic draining of the sump space; a water sensor coupled to the sump space that is used to periodically activate the drain; and at least one UVC light source configured for illuminating the water sensor within the sump space.

The sump of a water coalescing filter according to the invention may provide wherein at least one UVC light source is integrated with the water sensor and formed in a sensor body and directed at sensor probes, and wherein the UVC light source is integrated with the water sensor has light directed through a UVC trans-missive body.

The sump of a water coalescing filter according to the invention may provide wherein the at least one UVC light source is configured to be operated intermittently and wherein a plurality of UVC light sources are provided.

One aspect of this invention is directed to a sump of a water coalescing filter including a sump space, a drain coupled to the sump space for periodic draining of the sump space, a water sensor coupled to the sump space that is used to periodically activate the drain and at least one UVC light source configured for illuminating the water sensor within the sump space.

One aspect of the present invention is also directed to anti-biofouling in a reservoir for a fuel, hydraulic fluid, or industrial fluid which includes a reservoir space and sterilization zone or sump space as a lower portion of the reservoir space, preferably a drain is coupled to the sterilization zone for periodic draining of the sterilization zone, a water sensor coupled to the sterilization zone that is used to periodically activate the drain and at least one UVC light source configured for illuminating the fluid within the sterilization zone.

The features that characterize the present invention are pointed out with particularity in the claims which are part of this disclosure. These and other features of the invention, its operating advantages and the specific objects obtained by its use will be more fully understood from the following detailed description in connection with the attached FIGURES.

BRIEF DESCRIPTION OF THE FIGURES

FIG. 3 illustrates a UVC light source used for illuminating the water sensor or water in the embodiments of the present invention;

FIG. 4 schematically illustrates an anti-biofouling reservoir in accordance with one embodiment of the present invention;

FIGS. 5A and 5B schematically illustrate Water in Fuel sensors with integrated anti-biofouling UVC light source in accordance with two embodiments of the present invention.

DESCRIPTION OF THE PREFERRED EMBODIMENTS

Figure 1A:
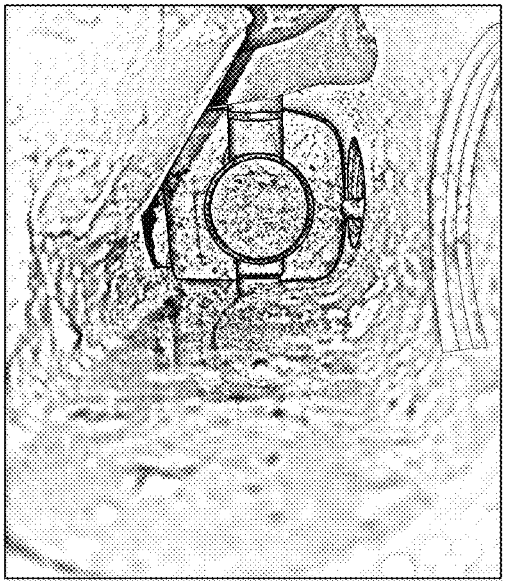
Prior Art FIG. 1A
FIG. 1A shows biofouling in a conventional sump space.
Figure 1B:
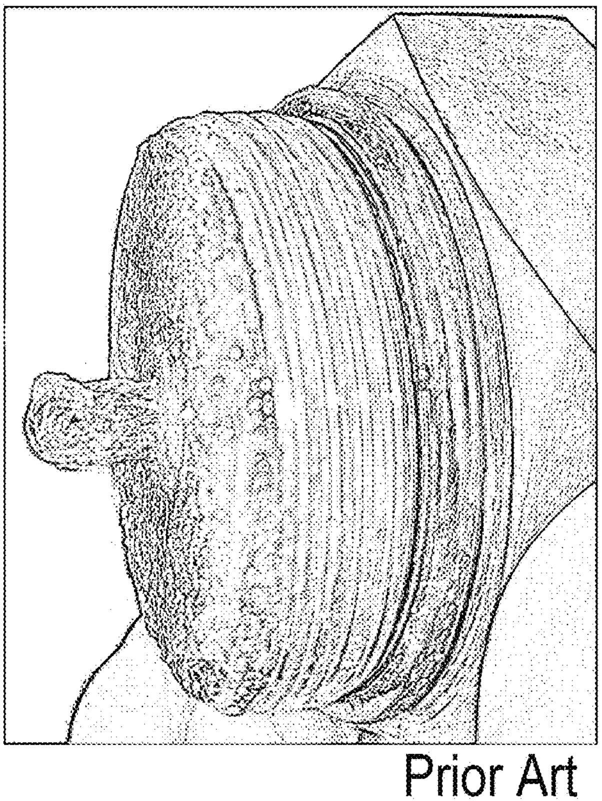
Prior Art FIG. 1B
FIG. 1B shows conventional biofouling of a sump based water in fuel (WIF) sensor preventing proper operation of the same.
Figure 2:
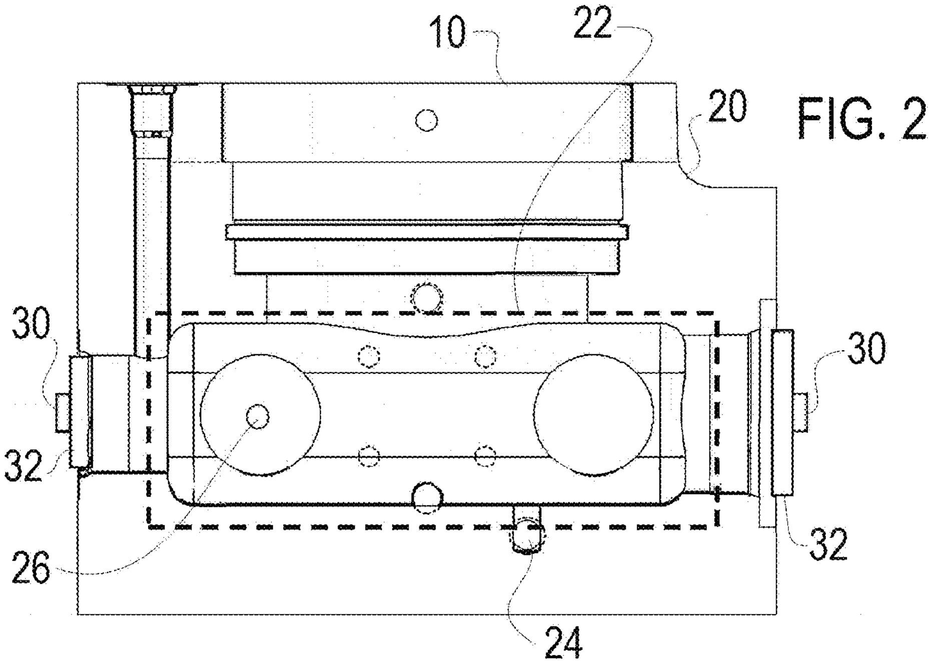
FIG. 2 schematically illustrates an anti-biofouling sump of a water coalescing filter in accordance with one embodiment of the present invention.

One aspect of this invention is shown schematically in FIG. 2 and is directed to a sump 20 of a water coalescing filter 10 including a sump space 22, a drain 24 coupled to the sump space 22 for periodic draining of the sump space 22, a water sensor 26 coupled to the sump space 22 that is used to periodically activated the signal operation of the drain 24, and at least one UVC light source 30 configured for illuminating the water sensor 26 within the sump space 20. FIG. 2 shows two UVC light sources 30 each mounted on a clear window or sight glass 32.

The water coalescing filter 10 may for a fuel, hydraulic fluid or industrial fluid. Suitable water coalescing filters 10 are available from the applicant Schroeder Industries. The water separated from the fuel, hydraulic fluid or industrial fluid will flow to a sump space 22 as known in the art. The sump space 22 is also called a basin, pan, tank, and reservoir and generally includes several ports (which may be threaded) for receiving accessories like the drain 24 and water level sensors 26. The use of threaded ports allows for easy modification of the sump 20.

The drain 24 coupled to the sump space 22 of the sump 20, typically within a port, is for periodic draining of the sump space 22. The drain 24 may be a simple valve that is opened and gravity used to drain the sump space 22. Alternatively, the drain 24 may further include a pump where a gravity drainage is not possible. The details of the valve (with or without a supplemental pump) are conventional and not shown in detail.

The water level sensor 26 is coupled to the sump space 22 of the sump 20, typically within a port, and is used to periodically activate the drain 24. The water level sensor 26 is a WIF (Water In Fuel) sensor which utilizes two metallic probes 36 separated by a short distance which creates an open circuit and which normally signals an "open" circuit. When the probes 36 are exposed to water, the signal passes through the water and closes the circuit which signals the presence of water, as water is more conductive than fuel or industrial fluids. The probes 36 of the WIF sensor 26 are extending into the sump space 22 at a level such that when water is sensed the drain 24 will be activated for a limited time to drain the sump space 22. The WIF sensor 26 generally detects the presence of the water/fluid interface which is at the upper level of the water in the sump space 22.

The WIF sensor 26 is coupled to a conventional controller (not shown) which operates the drain 24 when signaled and the system resets. The controller can also send signals to a display panel to indicate the change in operational status, and record an operational history, and/or send an alarm to indicate water level and drain 24 operation. The controller and specific control of the drain 24 is not shown in detail and is generally known in the art.

The sump 20 of the present invention incorporates an Anti-Biofouling System in the form of at least one UVC light source 30 configured for illuminating the WIF sensor 26 within the sump space 22. UVC light of the UVC light source 30 is in the range of 200 nm to 280 nm. UVC light has disinfecting properties in water, and it should be noted that UVC radiation has effectively been used for decades to reduce the spread of bacteria, such as tuberculosis. For this reason, UVC lamps in UVC light source 30 are often called "germicidal" lamps. UV radiation disrupts the chemical bonds that hold the atoms of DNA together in the microorganism. When the damage is severe enough the cells die.

The UVC light of the UVC light source 30 in the present invention is a 12 volt LED light in the UVC wavelength, such as the UVC light source 30 shown in FIG. 3. These LED lights have lower power consumption and long life and an effective range of about 6 inches. A 24 volt LED may be used. The Anti-Biofouling System may include additional UVC light sources 30 that are directed at the sump space 22, such as the two shown in FIG. 2. The added UVC light sources 30 do not all have to be directed at the sensor 26. As shown in FIG. 3, each UVC LED light source 30 is preferably outside of the sump space 22 and is directed through a transparent substrate referenced as a sight glass or window 32. The power supply and control of the UVC light sources 30 will easily be integrated into the control and power for the sensor 26 and the drain 24.

The Anti-Biofouling System described above supplies UVC light to the filter sump space 22 and the UVC light sterilizes the bacteria in the collected water and prevents growth. With no growth, the water sensor will operate properly and will drain the collected water and settled dead bacteria from the filter sump 20 properly. The UVC light is preferably supplied by efficient LED technology. Initial testing of the present invention demonstrated that the UV sterilized sample water had been essentially clarified, with dead bacteria at bottom of the test space.

The UVC LED light sources 30 will have an operating life of over 20,000 hours, so they could be left on for continuous operation. The disinfecting time for a typical sump space 22 with two opposed UVC LED based light source 30 would be less than ten minutes. As a solid-state device, UV-C LEDs can be cycled on/off tens of thousands of times with little or no observable difference or degradation in performance. UV-C LEDs also offer a near-instant capability to provide full rated output, requiring no warmup time. These abilities mean that LEDs can be employed in an on-demand fashion, accumulating operating hours only when "on" and providing their disinfection function without penalty. For example, operating intermittently at a period of 15 minutes every two and ½ hours would increase the effective life by an order of magnitude.

The Anti-Biofouling System described above is easily retrofitted into existing sumps 20 of a water coalescing filter 10 for a fuel, hydraulic fluid or industrial fluid. In such retrofitting operations one or two ports of the sump 20 are supplied with the UVC light sources 30 as shown above via a window 32 and a suitable power supply powering the same, which typically will be the power supply for the other components of the sump 20.

The present invention is also directed to anti-biofouling in a reservoir 40 for a fuel, hydraulic fluid, or industrial fluid which is shown schematically in FIG. 4. The reservoir 40 of the present invention includes a reservoir space and sterilization zone 42 or sump space as a lower portion of the reservoir space, preferably a drain 24 is coupled to the sterilization zone 42 for periodic draining of the sterilization zone 42, a water sensor 26, particularly a WIF sensor, is coupled to the sterilization zone 42 that is used to periodically activate the drain 24 and at least one UVC light source 30 configured for illuminating the fluid within the sterilization zone 42. The WIF sensor 26 may also be positioned so as to be illuminated by the UVC light source 30 to provide for anti-biofouling of the sensor probes 36, although if the water in the sump space is sterilized this would generally act to prevent biofouling of the sensor 30.

The reservoir 40 may be optimized by a sloping bottom surface 44 to guide fluid to the sterilization zone 42. The sterilization zone 42 is sized to allow for sterilization of the entire zone 42 by the UVC light sources 30.

The water sensor 26 is used to operate the drain 24 and will prevent the water from accumulating beyond the sterilization zone 42 which could lead to bacterial growth and acetic acid accumulation due to such growth. As with the sump 20 discussed above, the drain 24 will drain off water and dead bacteria to prevent accumulation within the reservoir 40. The UVC light of the light source 30 is preferably supplied by efficient LED technology as discussed above and may be formed, installed and operated largely as described above. It is preferable if the UVC light sources 30 will illuminate the sensor 26 to prevent the biofouling of the water sensor 26.

The Anti-Biofouling System in a reservoir 40 described can be easily retrofitted into existing reservoirs 40 for a fuel, hydraulic fluid or industrial fluid where the sterilization zone 22 (and associated elements) can be coupled to a low point of the reservoir 40 where water will collect. For example some reservoirs have an existing drain in the low point of the reservoir 40 and The Anti-Biofouling System described above is coupled thereto with the existing or prior drain left open (or simply removed).

The applicants have verified the effectiveness of directing UVC light at the surface of the WIF sensor 26. A UVC LED was installed in the sump 20 of a water coalescing filter 10. Fuel was circulated through the filter 10 during weekdays for a few hours a day, and 1 liter of water was injected per day to simulate typical use of the filter in a normal application. This was tested for 25 days without the UVC sterilizer and drained for inspection upon completion. Then the sump 20 was cleaned and the test repeated for another 25 days in the same test circuit with the UVC sterilizer of the present invention installed. The results of this testing show that there is a significant reduction in the microbial growth on the WIF sensor 26 as well as a reduction in total microbial growth Thus it has been shown that illuminating the sensor 26 with UVC light from a UVC LED light source 30 significantly reduces or eliminates the microbial growth on the WIF sensor 26 and allows more reliable operation and reduced maintenance.

In order to provide a more compact product, and to eliminate the need for additional porting for multiple accessories (both the WIF sensor 26 and UVC LED light source 30) in sumps 30 reservoirs 40 and other applications, the UVC LED source 30 can be integrated directly into the WIF sensor 26 as shown in FIGS. 5A and 5B. This combined arrangement saves cost and eliminates a potential leakage point. The relatively new UVC LED technology provides a small enough light source 30 to integrate the LED into the WIF sensor 26 to provide the anti-biofouling UVC light directly to the WIF sensor probes 36.

As noted above the WIF (Water In Fuel) sensor 26 utilizes two metallic probes 36 separated by a short distance which creates an open circuit and which normally signals an "open" circuit. When the probes 36 are exposed to water, the signal passes through the water and closes the circuit which signals the presence of water, as water is more conductive than fuel or industrial fluids. The WIF sensors 26 have been described as are solid-state devices designed to detect the presence or absence of water in fuel wherein each sensor 26 contains integral, high-temperature-rated electronics that generate an alternating voltage to a probe 36 tip, whereby the presence of water completes the circuit which, in turn, changes the condition of a transistor output. The power and associated control circuitry of WIF sensors 26 is known in the art and not shown in detail herein. The difference in the sensors 26 of FIGS. 5A and 5B is that the present invention provides a UVC LED light source 30 integrated directly into the body of the WIF sensor 26 in a position to illuminate the probes 36. FIG. 5A shows an embodiment in which the UVC LED source 30 is in the sensor 26 body and is directed at the probes 36. FIG. 5B shows an embodiment in which the UVC LED source 30 is in the sensor 26 body has light directed through a UVC trans-missive body 34 such as glass or plastic at the probes 36.

As noted above the UVC LED light sources 30 will have an operating life of over 20,000 hours, so they could be left on for continuous operation in the WIF sensor 26 of the invention and can be easily powered as well as cycled on and off (for intermittent use and longer life) by the controller for the sensor 26. The disinfecting time for a typical probe 36 pair of a WIF sensor 26 would be considerably less than a sump space 22 discussed above and thus cycle times of around two minutes once a day would be effective and yield exceptionally long life. As noted above the UV-C LEDs can be cycled on/off tens of thousands of times with little or no observable difference or degradation in performance. UV-C LEDs also offer a near-instant capability to provide full rated output, requiring no warmup time. These abilities mean that LEDs can be employed in an on-demand fashion, accumulating operating hours only when "on" and providing their disinfection function without penalty.

While the invention has been shown in several particular embodiments it should be clear that various modifications may be made to the present invention without departing from the spirit and scope thereof. The scope of the present invention is defined by the appended claims and equivalents thereto.

What is claimed is:

1. An anti-biofouling reservoir for a fuel, hydraulic fluid, or industrial fluid comprises:

a reservoir space, sterilization zone as a lower portion of the reservoir space, wherein a bottom surface of the reservoir space is sloped to guide fluid to the sterilization zone, a drain is coupled to the sterilization zone for periodic draining of the sterilization zone, a water sensor coupled to the sterilization zone that is used to periodically activate the drain, wherein the water sensor is positioned below the sloped bottom surface of the reservoir and is a water-in-fuel sensor configured to detect the interface of water and the fuel, hydraulic fluid, or industrial fluid and at least one UVC light source configured for illuminating the fluid within the sterilization zone wherein the at least one UVC light source is positioned below the sloped bottom surface of the reservoir.

2. The anti-biofouling reservoir for a fuel, hydraulic fluid, or industrial fluid according to claim 1 wherein the water sensor includes sensor probes positioned so as to be illuminated by at least one UVC light source to provide for anti-biofouling of the sensor probes.

3. The anti-biofouling reservoir for a fuel, hydraulic fluid, or industrial fluid according to claim 2 wherein the sterilization zone is sized to allow for sterilization of the entire zone by the at least one UVC light source.

4. The anti-biofouling reservoir for a fuel, hydraulic fluid, or industrial fluid according to claim 3 wherein the at least one UVC light source is configured to be operated intermittently.

5. The anti-biofouling reservoir for a fuel, hydraulic fluid, or industrial fluid according to claim 4 wherein at least one UVC light source is integrated with the water sensor and formed in a sensor body and directed at sensor probes.

6. The anti-biofouling reservoir for a fuel, hydraulic fluid, or industrial fluid according to claim 5 wherein the UVC light source has light directed through a UVC trans-missive body.

7. The anti-biofouling reservoir for a fuel, hydraulic fluid, or industrial fluid according to claim 1 wherein the sterilization zone is sized to allow for sterilization of the entire zone by the at least one UVC light source.

8. The anti-biofouling reservoir for a fuel, hydraulic fluid, or industrial fluid according to claim 1 wherein the at least one UVC light source is configured to be operated intermittently.

9. An anti-biofouling reservoir for a fuel, hydraulic fluid, or industrial fluid comprises:

a reservoir space, sterilization zone as a lower portion of the reservoir space, a drain is coupled to the sterilization zone for periodic draining of the sterilization zone, a water sensor coupled to the sterilization zone that is used to periodically activate the drain, and at least one UVC light source configured for illuminating the fluid within the sterilization zone, wherein at least one UVC light source is integrated with the water sensor and formed in a sensor body and directed at sensor probes.

10. The anti-biofouling reservoir for a fuel, hydraulic fluid, or industrial fluid according to claim 9 wherein the UVC light source has light directed through a UVC trans-missive body.

11. A sump of a water coalescing filter configured for separating water from fuel, hydraulic fluid, or industrial fluid comprising:

a sump space receiving fluid from the water coalescing filter;

a drain coupled to the sump space for periodic draining of the fluid in the sump space;

a water sensor coupled to the sump space that is used to periodically activate the drain, wherein the water sensor is a water-in-fuel sensor configured to detect the interface of water and the fuel, hydraulic fluid, or industrial fluid in the fluid within the sump space; and at least one UVC light source configured for illuminating the water sensor within the sump space.

12. The sump of a water coalescing filter according to claim 11 wherein at least one UVC light source is integrated with the water sensor and formed in a sensor body and directed at sensor probes.

13. The sump of a water coalescing filter according to claim 12 wherein the UVC light source has light directed through a UVC trans-missive body.

14. The sump of a water coalescing filter according to claim 13 wherein the at least one UVC light source is configured to be operated intermittently.

15. The sump of a water coalescing filter according to claim 11 wherein a plurality of UVC light sources are provided.

16. The sump of a water coalescing filter according to claim 11 wherein the UVC light source is integrated with the water sensor and has light directed through a UVC trans-missive body.

17. The sump of a water coalescing filter according to claim 16 wherein the at least one UVC light source is configured to be operated intermittently.

18. The sump of a water coalescing filter according to claim 11 wherein the at least one UVC light source is configured to be operated intermittently.

* * * * *